United States Patent [19]

Johnson

[11] Patent Number: 4,671,857

[45] Date of Patent: Jun. 9, 1987

[54] METHOD FOR SEPARATING METHACRYLIC ACID FROM ISOBUTYRIC ACID

[75] Inventor: Kris A. Johnson, Longview, Tex.

[73] Assignee: Eastman Kodak Company, Rochester, N.Y.

[21] Appl. No.: 911,696

[22] Filed: Sep. 26, 1986

[51] Int. Cl.$^4$ .................. B01D 3/34; C07C 51/44
[52] U.S. Cl. .................................. 203/51; 203/60; 203/DIG. 21; 562/599; 562/600
[58] Field of Search ............... 203/60, 51, DIG. 21, 203/38; 562/600, 599

[56] References Cited

U.S. PATENT DOCUMENTS

| | | | |
|---|---|---|---|
| 3,414,485 | 12/1968 | Speed | 562/599 |
| 3,663,375 | 5/1972 | Witheford | 562/600 |
| 4,142,058 | 2/1979 | Matsumura et.al. | 203/DIG. 21 |
| 4,600,795 | 7/1986 | Frank | 562/60 |

Primary Examiner—Wilbur Bascomb
Attorney, Agent, or Firm—William P. Heath, Jr.; J. Frederick Thomsen

[57] ABSTRACT

The distillative separation of methacrylic acid from isobutyric acid is significantly improved by the introduction into the distillation system of a third component selected from the group consisting of methyl methacrylate, methyl isobutyrate and dimethylformamide.

4 Claims, No Drawings

METHOD FOR SEPARATING METHACRYLIC ACID FROM ISOBUTYRIC ACID

This invention concern improvements in the separation of isobutyric acid from methacrylic acid by distillation.

PRIOR ART

A commonly used process for the manufacture of methacrylic acid is the catalytic dehydrogenation of isobutyric acid (IBA) to methacrylic acid (MAA) wherein the IBA is vaporized in the presence of oxygen and contacted at a temperature in the range of 250° C.–600° C. with a suitable catalyst. The product obtained from this dehydrogenation reaction comprises a mixture of isobutyric acid, methacrylic acid and water. Following the separation of the acids from the water the remaining mixture of the two acids which are very similar in structure and other physical properties is very difficult to separate by distillation. Also, the tendency of the MAA to polymerize under distillation conditions further complicates the matter. A further complication to the separation of the two acids is the dimeric nature of carboxylic acids, both in the liquid and vapor state. Such dimerization through the carboxyl groups is described in ORGANIC CHEMISTRY, THIRD EDITION, R. T. MORRISON and R. N. BOYD, ALLYN AND BACON, INC., 1974, page 582, and other textbooks. With carboxylic acids of such similar properties and molecular weight, there is little discrimination and dimers IBA-IBA, MAA-MAA and IBA-MAA are all formed. With such indiscriminate dimer formation, poor distillation efficiencies result.

Attempts to overcome this problem by axeotroping has required complex separating techniques for removing the azeotroping agent from the product, while attempts employing extractive distillation using complexing agents raised the base temperature of the column wherein the methacrylic acid was heated to a point which resulted in high yield loss due to polymerization.

SUMMARY OF THE INVENTION

A method for the distillative separation of methacrylic acid from isobutyric acid comprising feeding to a distillation column a mixture of methacrylic acid isobutyric acid and a third component selected from at least one of methyl methacrylate, methyl isobutyrate or dimethylformamide, said third component being fed in an amount effective to increase the efficiency of the distillative separation. The effective amount of said third component is a volumetric feed ratio of third component to mixed acid feed of about 0.5 to about 3.0. A volumetric feed ratio is from about 1.0 to about 2.5 and is preferred.

Methyl methacrylate is the preferred third component.

The method of this invention uses a third component which apparently has the effect of increasing the vapor pressure of the isobutyric acid more than that of the methacrylic acid without forming an azeotrope or a complex in the classical sense. Thus, both the overhead isobutyric acid and the remaining methacrylic acid each can be separated from the third component by ordinary distillation. My invention therefore provides a more economical and practical method for separating heat-sensitive methacrylic acid from isobutyric acid.

In previous schemes for making the separation, a distillation column operating at a high vacuum would require in excess of 100 plates. The present process on the other hand utilizes a conventional distillation column of, for example, 30–50 plates wherein the mixed acid feed stream is injected at a point approximately midway up the column. The third component used in accordance with this invention is at least one of methyl methacrylate, methyl isobutyrate and dimethylformamide fed to the column, preferably the base, at a rate of maintain a volumetric feed ratio of third component to mixed acid feed which will be effective for the particular type and size of column being used. For the type and size of multi-plate column described below in Example 1, a ratio of from about 0.5 to about 3.0, and particularly from about 1.5 to about 2.5 is desirable. The column is otherwise operated in conventional manner.

The present invention is illustrated in more detail by the following examples, but it will be understood that these examples are illustrative only and are not intended to limit the scope of the invention in any manner.

EXAMPLE 1

A two-inch diameter 45 plate Oldershaw distillation column is equipped with a condensed liquid reflux splitter. Column feed is 15 plates from the bottom with 50/50 weight percent of isobutyric and methacrylic acids at a rate of 300 ml of the mixed acid per hour. After column operation has been stabilized it is found that the overhead product contains by weight 90.41% isobutyric acid and 9.59% methacrylic acid, and the base product contains 11.04% isobutyric acid and 88.96% methacrylic acid. This gives a calculated plate efficiency of 51%. Following column stabilization, the mixed acid feed rate is cut from 300 ml/hour to 60 ml/per hour and methyl methacrylate is started to the base at 120 ml per hour. Mixed acid and methyl methacrylate feed rates are maintained such that the same loading is experienced in the top of the column as exists without methyl methacrylate feed. The volumetric ratio of methyl methacrylate to mixed acid feed is maintained at about 2:1. After the column has again stabilized the overhead product is analyzed to contain 79.18% methyl methacrylate, 20.56% isobutyric acid and 0.26% methacrylic acid whereas the base product contains 0.77% methyl methacrylate, 6.57% isobutyric acid and 92.66% methacrylic acid. This calculates out to a plate efficiency of 89%.

In like manner runs are made using dimethylformamide, normal heptane, chlorobenzene, normal butylacetate and methyl isobutyrate as the third component with a volumetric feed ratio of third component to mixed acid feed in each case of 2:1. The calculated plate efficiencies obtained are as follows: dimethylformamide-79.3% and chlorobenzene-56.6%. It is noted that 51% efficiency is obtained with no third component present indicating, for example, that chlorobenzene was essentially inactive. In another run using methyl methacrylate, the volumetric feed ratio, of third component to mixed acid feed, was dropped to 1.0 and produced a calculated plate efficiency of 83.0%.

EXAMPLE 2

A one-inch 60-plate Oldershaw distillation column was fed a 50–50 weight percent solution of methacrylic and isobutyric acid with no low boiler being added to the base. The separation achieved was used as a basis for comparison to the later separations made with low boiler being added to the base. The resultant separation with no low boiler being added was:

|  | Top | Base |
|---|---|---|
| i-HOBu | 87.81 | 15.67 |
| MAA | 12.19 | 84.33 |
|  | 100.00 | 100.00 |

This calculates out to a plate efficiency of 32%. After the above data point was collected, the mixed acid feed rate was cut from 200 ml/hr to 90 ml/hr and a feed rate of 100 ml/hr of methyl methacrylate was started. This gave a feed ratio of 1.11 methyl methacrylate to mixed acid feed. The top and base compositions obtained under these conditions were:

|  | Top | | Base | |
|---|---|---|---|---|
|  | Based On Acids Only | Actual Comp. | Based On Acids Only | Actual Comp. |
| MMA | — | 43.93 | — | 0.77 |
| i-HOBu | 88.36 | 49.55 | 10.19 | 10.11 |
| MAA | 11.64 | 6.52 | 89.81 | 89.12 |
|  | 100.00 | 100.00 | 100.00 | 100.00 |

This amounted to a 37 percent plate efficiency.

Methyl isobutyrate was used as the next low boiling feed. The mixed acid feed was cut from 90 ml/hr to 70 ml/hr and a feed rate of 110 ml/hr of methyl isobutyrate. This amounts to a methyl isobutyrate to mixed acid feed ratio of 1.57. The following separation was achieved.

|  | Top | | Base | |
|---|---|---|---|---|
|  | Based On Acids Only | Actual Comp. | Based On Acids Only | Actual Comp. |
| MMA | — | 39.90 | — | 0.66 |
| i-HOBu | 94.23 | 56.63 | 14.15 | 14.06 |
| MAA | 5.77 | 3.47 | 85.85 | 85.28 |
|  | 100.00 | 100.00 | 100.00 | 100.00 |

This amounted to a plate efficiency of 42 percent.

The two-inch diameter 45-plate distillation column described and used in Example 1 inherently has a higher efficiency than does the one-inch diameter 60-plate distillation column described and used in Example 2. The two-inch column is easier to operate because lower loadings can be used. This gives a lower ΔP per plate in the two-inch column than the one-inch column. Also, the plates in the two-inch column are spaced further apart making it resistant to foam getting started and then travelling from plate to plate. The significant increases in plate efficiency in the two-inch column over that of the one-inch column is believed to result from a combination of the longer diameter and greater plate spacing in the two-inch column coupled with the higher methyl methacrylate to mixed acid feed rate.

Although the invention has been described in considerable detail with reference to certain preferred embodiments thereof, it is understood that variations and modifications can be effected without departing from the spirit and scope of the invention as described hereinabove and in the appended claims.

I claim:

1. A method for the distillative separation of methacrylic acid from isobutyric acid comprising feeding to a distillation column a mixture of methacrylic acid, isobutyric acid and a third component selected from at least one of methyl methacrylate, methyl isobutyrate or dimethylformamide, said third component being fed in an amount sufficient to increase the efficiency of the distillative separation.

2. Method of claim 1 wherein the effective amount of said third component is a volumetric feed ratio of third component to mixed acid feed of about 0.5 to about 3.0.

3. The process of claim 1 wherein the said volumetric feed ratio is from about 1.0 to about 2.5

4. The process of claim 1 wherein the third component is methyl methacrylate.

* * * * *